United States Patent
Neumann

(10) Patent No.: US 12,362,058 B2
(45) Date of Patent: Jul. 15, 2025

(54) APPARATUS AND METHOD FOR USING A FEEDBACK LOOP TO OPTIMIZE MEALS

(71) Applicant: KPN INNOVATIONS, LLC., Lakewood, CO (US)

(72) Inventor: Kenneth Neumann, Lakewood, CO (US)

( * ) Notice: Subject to any disclaimer, the term of this patent is extended or adjusted under 35 U.S.C. 154(b) by 1 day.

(21) Appl. No.: 18/410,848

(22) Filed: Jan. 11, 2024

(65) Prior Publication Data

US 2024/0249815 A1    Jul. 25, 2024

Related U.S. Application Data

(63) Continuation-in-part of application No. 18/100,035, filed on Jan. 23, 2023, now Pat. No. 11,887,720.

(51) Int. Cl.
   *G16H 20/60* (2018.01)
   *G06F 40/40* (2020.01)

(52) U.S. Cl.
   CPC ............. *G16H 20/60* (2018.01); *G06F 40/40* (2020.01)

(58) Field of Classification Search
   CPC .............................. G09B 19/0092; G16H 20/60
   See application file for complete search history.

(56) References Cited

U.S. PATENT DOCUMENTS

| | | |
|---|---|---|
| 2014/0141983 A1 | 5/2014 | Singh et al. |
| 2018/0240542 A1 | 8/2018 | Grimmer et al. |
| 2019/0304000 A1* | 10/2019 | Simpson ............... G16B 40/00 |
| 2020/0066181 A1 | 2/2020 | Hadjigeorgiou et al. |
| 2020/0131581 A1 | 4/2020 | Jain et al. |
| 2021/0042637 A1 | 2/2021 | Neumann |
| 2021/0065873 A1 | 3/2021 | Wolf et al. |
| 2021/0241881 A1 | 8/2021 | Avery et al. |
| 2021/0265036 A1* | 8/2021 | Lynn ...................... G16H 50/20 |
| 2021/0304868 A1 | 9/2021 | Neumann |
| 2022/0005580 A1 | 1/2022 | Pavlov et al. |
| 2022/0215930 A1 | 7/2022 | Eshel et al. |

* cited by examiner

*Primary Examiner* — Peter R Egloff

(74) *Attorney, Agent, or Firm* — Caldwell Intellectual Property Law

(57) ABSTRACT

The present disclosure is generally directed to an apparatus for using a feedback loop to optimize meals, may include at least a processor; and a memory communicatively connected to the processor, the memory containing instructions configuring the at least a processor to retrieve nutrition data from a database. The processor may be configured to generate an optimization score, wherein generating the optimization score may include training an optimization machine-learning model, wherein the optimization machine-learning model is trained with optimization training data, inputting a nutrient quantity to the optimization machine-learning model to output a target nutrient score, and generating an optimization score as a function of the nutrition data and the target nutrient score.

20 Claims, 8 Drawing Sheets

APPARATUS AND METHOD FOR USING A FEEDBACK LOOP TO OPTIMIZE MEALS

CROSS-REFERENCE TO RELATED APPLICATIONS

This application is a continuation-in-part of Non-provisional application Ser. No. 18/100,035 filed on Jan. 23, 2023, and entitled "AN APPARATUS AND METHOD FOR USING A FEEDBACK LOOP TO OPTIMIZE MEALS," the entirety of which is incorporated herein by reference.

FIELD OF THE INVENTION

The present invention generally relates to the field of nutrients and nutritional recipes. In particular, the present invention is directed to an apparatus and method for using a feedback loop to optimize meals.

BACKGROUND

Many factors may need to be accounted for when preparing a meal. However, many of these factors are unoptimized across a range of phenotypes. Further, many factors may change over time for a specific meal and/or phenotype.

SUMMARY OF THE DISCLOSURE

In an aspect, an apparatus for using a feedback loop to optimize meals is disclosed. The apparatus includes at least a processor and a memory communicatively connected to the processor, the memory containing instructions configuring the at least a processor to retrieve nutrition data from a database, generate a nutrient target score as a function of the nutrition data, generate an optimization score as a function of the nutrition data and the nutrient target score, generate an edible chain as a function of the nutrition data and the target nutrient score, wherein the edible chain includes a plurality of ranked edible elements and generating the edible chain includes generating chain training data, wherein the chain training data includes correlations between exemplary nutrition data, exemplary target nutrient scores and exemplary edible chains, training a chain machine-learning model using the chain training data and generating the edible chain using the trained chain machine-learning model and update the edible chain as a function of a user input received through a user interface, wherein updating the edible chain includes iteratively updating the chain training data on a feedback loop as a function of the updated edible chain.

In another aspect, a method for using a feedback loop to optimize meals includes retrieving, using at least a processor, nutrition data from a database, generating, using the at least a processor, a nutrient target score as a function of the nutrition data, generating, using the at least a processor, an optimization score as a function of the nutrition data and the nutrient target score, generating, using the at least a processor, an edible chain as a function of the nutrition data and the target nutrient score, wherein the edible chain comprises a plurality of ranked edible elements and generating the edible chain includes generating chain training data, wherein the chain training data includes correlations between exemplary nutrition data, exemplary target nutrient scores and exemplary edible chains, training a chain machine-learning model using the chain training data and generating the edible chain using the trained chain machine-learning model and updating, using the at least a processor, the edible chain as a function of a user input received through a user interface, wherein updating the edible chain includes iteratively updating the chain training data on a feedback loop as a function of the updated edible chain.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods for using a feedback loop to optimize meals. In an embodiment, a feedback loop may be initiated by continuously collecting nutrient data for a phenotype over a time interval. The collected data may be compared to previously collected data to determine whether any changes need to be made to any meals.

In some embodiments, an apparatus includes at least a processor and a memory communicatively connected to the processor, the memory containing instructions configuring the at least a processor to retrieve nutrition data from a database, generate a nutrient target score as a function of the nutrition data, generate an optimization score as a function of the nutrition data and the nutrient target score, generate an edible chain as a function of the nutrition data and the target nutrient score, wherein the edible chain includes a plurality of ranked edible elements and generating the edible chain includes generating chain training data, wherein the chain training data includes correlations between exemplary nutrition data, exemplary target nutrient scores and exemplary edible chains, training a chain machine-learning model using the chain training data and generating the edible chain using the trained chain machine-learning model and update the edible chain as a function of a user input received through a user interface, wherein updating the edible chain includes iteratively updating the chain training data on a feedback loop as a function of the updated edible chain.

Aspects of the resent disclosure allow for continuous optimization of meals as a function nutrition data for a user or phenotype. Exemplary embodiments illustrating aspects of the present disclosure are described below in the context of several specific examples.

Figure 1:
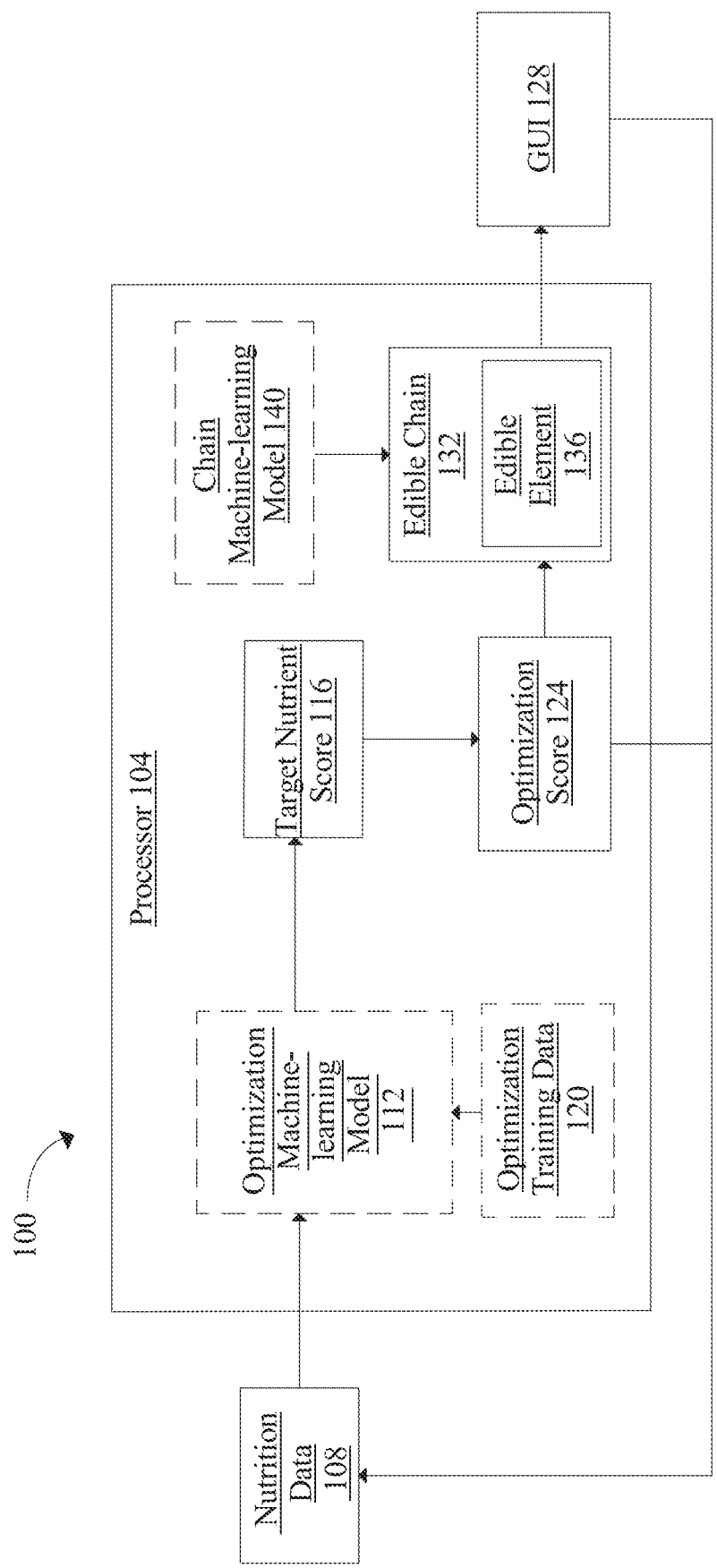
FIG. 1 is a block diagram of an exemplary embodiment of an apparatus for using a feedback loop to optimize meals.

Referring now to FIG. 1, an exemplary embodiment of an apparatus 100 for generating scoring a nutrient is illustrated. Apparatus 100 may include a computing device. Apparatus 100 may include a processor and a memory communicatively connected to the processor. A memory may include instructions configuring at least a processor to perform various tasks. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Still referring to FIG. 1, in some embodiments, apparatus 100 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Apparatus 100 may include a single computing device operating independently, or may include two or more computing device operating in concert, in parallel, sequentially or the like; two or more computing devices may be included together in a single computing device or in two or more computing devices. Apparatus 100 may interface or communicate with one or more additional devices as described below in further detail via a network interface device. Network interface device may be utilized for connecting apparatus 100 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Apparatus 100 may include but is not limited to, for example, a computing device or cluster of computing devices in a first location and a second computing device or cluster of computing devices in a second location. Apparatus 100 may include one or more computing devices dedicated to data storage, security, distribution of traffic for load balancing, and the like. Apparatus 100 may distribute one or more computing tasks as described below across a plurality of computing devices of computing device, which may operate in parallel, in series, redundantly, or in any other manner used for distribution of tasks or memory between computing devices. Apparatus 100 may be implemented using a "shared nothing" architecture in which data is cached at the worker, in an embodiment, this may enable scalability of apparatus 100 and/or computing device.

With continued reference to FIG. 1, apparatus 100 may be designed and/or configured to perform any method, method step, or sequence of method steps in any embodiment described in this disclosure, in any order and with any degree of repetition. For instance, apparatus 100 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Apparatus 100 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, apparatus 100 may be configured to receive nutrition data 108. As used in this disclosure, "nutrition data" is information relating to the nutrition of an individual or a phenotype group. Nutrition data 108 may include a biological extraction. A "biological extraction" as used in this disclosure includes at least an element of user physiological data. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. In some embodiments, user data may include physiological data.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C (HbA1c) levels. Physiological state data may include, without limitation, one or more measures associated with endocrine function, such as without limitation, quantities of dehydroepiandrosterone (DHEAS), DHEA-Sulfane, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module as described in this disclosure.

Still referring to FIG. 1, physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which, as used herein, is data describing all proteins produced and/or modified by an organism, colony of organisms, or system of organisms, and/or a subset thereof. Physiological state data may include data concerning a microbiome of a person, which, as used herein, includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation, any result of any medical test, physiological assessment, cognitive assessment, psychological assessment, or the like. Apparatus 100 may receive at least a physiological data from one or more other devices after performance; apparatus 100 may alternatively or additionally perform one or more assessments and/or tests to obtain at least a physiological data, and/or one or more portions thereof, on apparatus 100. For instance, at least physiological data may include or more entries by a user in a form or similar graphical user interface object; one or more entries may include, without limitation, user responses to questions on a psychological, behavioral, personality, or cognitive test. For instance, at least a server may present to user a set of assessment questions designed or intended to evaluate a current state of mind of the user, a current psychological state of the user, a personality trait of the user, or the like; at least a server may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

Still referring to FIG. 1, nutrition data 108 may include nutrient data. As used in this disclosure, "nutrient data" is information relating to nutrients of a meal. In some embodiments, nutrient data may include a nutrient quantity of a meal. As used in this disclosure, "nutrient quantity" is an amount of a nutrient within a meal or recipe. In some instances, nutrient quantity may be measured in terms of weight. As a non-limiting example, nutrient quantity may be in grams, milligrams, kilograms, or the like. In some embodiments, nutrition data 108 may include an average nutrient optimization across phenotypes and/or clusters of phenotypes. As used in this disclosure, "phenotype" is any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence.

With continued reference to FIG. 1, in some embodiments, nutrition data 108 may include a nutrient score. As used in this disclosure, a "nutrient score" is a value given to a nutrient. A nutrient classifier may be used to generate a nutrient score. A nutrient classifier may score plurality of nutrients across a plurality of phenotypes. In some instances, nutrient classifier may be trained using nutrient classifier training data. In some embodiments, nutrient classifier training data may include historical nutrient data correlated to categories of nutrients. In some embodiments, nutrient classifier training data may contain categories of nutrients correlated to scores for those categories of nutrients. In some embodiments, a lookup table correlating categories of nutrients to nutrient scores may be used to determine a nutrient score once nutrient classifier determines a category of nutrient. In some embodiments, a nutrient classifier may be configured to score a plurality of nutrients of plurality of nutrients. Nutrient scores may be based off, without limitation, relative impact of one or more nutrients on one or more phenotypes. For instance, and without limitation, a score of 6 out of 10 may be assigned to a filet mignon for a phenotype of vegan. In some embodiments, a score may be based off a target nutrient range. In some embodiments, nutrient score may be generated by using an objective function as described in further detail below. It should be noted that the nutrient score may be generated using an objective function that is optimized using impact factors as constraints. In some instances, objective function may be optimized using phenotype groupings as constraints. Nutrient classifier may be consistent with disclosure of nutrient classifier in U.S. patent application Ser. No. 18/090,411, filed on Dec. 28, 2022, and entitled "APPARATUS AND METHOD FOR SCORING A NUTRIENT," which is incorporated herein by reference.

Still referring to FIG. 1, nutrition data 108 may include a nutrition score. As used in this disclosure, a "nutrition score," as used in this definition, is data, including any character, symbolic, and/or numerical data, reflecting the current overall nutritional impact of a specific meal, snack, or drink for a specific grouping of typical body types and current conditions. A nutritional score may be transient and/or dynamic and varies automatically with ingredients utilized, recipe, cooking instructions, storage impacts, meal, drink or snack size, or the like. A nutritional score may be graded on a continuum, where a score of zero may indicate a meal/drink which is in extremely poor for nutritional health while a score of 100 may indicate a meal/drink which is excellent for nutritional health. A negative nutritional score would reflect that an item has no beneficial impact and actually has a net detrimental impact. In cases of negative impact, the item will score as "negative impact" with no numerical assignment. Processor 104 may retrieve nutrition score from a database. In some embodiments, database may be stored locally or remotely. It should be noted that nutrition score may be associated with a particular user. In some instances, nutrition score may be associated with a particular meal for a particular user. In some instances, nutrition score may be associated with a particular nutrient for a particular user, across a plurality of meals. Nutrition data 108 may include nutrition data for a plurality of users. In some embodiments, the plurality of users may share a characteristic, such as a phenotype. In some embodiments, nutrition data may include nutrition data appertaining to a plurality of users including a plurality of phenotypes.

Still referring to FIG. 1, nutrition data 108 may include a vibrant health score. As used in this disclosure, a "vibrant health score" as used in this definition, is data, including any character, symbolic, and/or numerical data, reflecting the current state of a user's integrated and overall health considering assessment of all currently possible variables. Currently possible variables will include nourishment score, whole body wellness analysis including all possible variables, assessment and status across top 100 age related degradation factors, current root cause analysis, prevention, and reversal status of every diagnosed disease and at least one year of active participation producing reliable and comprehensive data for analysis.

With continued reference to FIG. 1, nutrition data 108 may include a nourishment score. As used in this disclosure, a "nourishment score," as used in this definition, is data, including any character, symbolic, and/or numerical data, reflecting the current overall nutritional state of a user. Nourishment score may be transient and/or dynamic. A nourishment score may be graded on a continuum, where a score of zero may indicate a user who is in extremely poor nutritional health while a score of 100 may indicate a user who is in excellent nutritional health. A nourishment score may be calculated from one or more factors that may be stored within a database containing items such as food intake, water intake, supplement intake, prescription medication intake, fitness practice, health goals, chronic health conditions, acute health conditions, spiritual wellness, meditation practice, stress levels, love/friendship status, purpose and values congruency, levels of joy and peace, gratitude mindset, body restoration coefficients, and the like. A nourishment score may be updated based on one or more meals that a user consumed and/or is planning to consume or any of the factors just listed.

Still referring to FIG. 1, nutrition data 108 may include a meals environmental score. As used in this disclosure, a "meals environmental score" is a combined analysis of source of ingredients, distance ingredients were moved from harvest to consumption, impact ingredient production directly had on the environment including, soils deterioration, pesticides usage, carbon production, water consumption, etc., local sourcing, seasonal availability, quality and purity of ingredients, and other possible items that have substantial impact. The impact to and treatment of animals will also be integrated with this score but in ways that allows the religious impact of the vegan mindset to separate itself.

Continuing to refer to FIG. 1, nutrition data 108 may be based on a geofenced area. As used in this disclosure, a "geofenced area" is a virtual perimeter surrounding a real-world geographic area. A geofence may be generated as a radius around a point or location or arbitrary borders drawn by a user. In some embodiments, the point or location may be selected by a user through user input, wherein user input may include, as non-limiting examples, tapping on a screen, inputting an address, inputting coordinates, and the like. A geofence additionally be generated to match a predetermined set of boundaries such as neighborhoods, school zones, zip codes, county, state, and city limits, area codes, voting districts, geographic regions, streets, rivers, other landmarks, and the like. In embodiments, geofences may be generated as a function of a user input. In some embodiments, nutrition data 108 may be truncated as a function of a geofenced area. As a non-limiting example, nutrition data 108 may only include meals with nutrients available in a geofenced area. In some embodiments, nutrition data 108 may include phenotypes of users within a geofenced area. This may augment target nutrient scores, however, processor 104 may correct for the truncated nutrition data 108 in order to generate optimization score 120. In some instances, processor 104 may correct truncated data by adding filler data entries. Filler data entries may be valueless. In some embodiments, filler data entries may be averages for a particular data entry over time. As a non-limiting example, filler data entries may include a general average nutrient score for a nutrient that may exceed the geographical bounds of a geofenced area.

Still referring to FIG. 1, nutrition data 108 may be used as an input to an optimization machine-learning model 112. As used in this disclosure, a "optimization machine-learning model" is a mathematical and/or algorithmic representation of a relationship between inputs and outputs. An optimization machine-learning model 112 may be implemented in any manner described in this disclosure regarding implementing and/or training machine-learning models. Inputs to optimization machine-learning model 112 may be any nutrition data 108 described in this disclosure. Outputs of optimization machine-learning model 112 may be a target nutrient score 116. As used in this disclosure, "target nutrient score" is a score for a nutrient that is recommended for an individual to consume. Scores may include numbers representing a maximal amount to be consumed, a minimal amount to be consumed, and/or a precise amount that is determined to be ideal. Scores may be zero for a nutrient that a user should not receive, and/or for a nutrient having no positive health benefit; for instance, a user who is diabetic may be recommended a quantity of zero for glucose, sucrose, or the like. Target nutrient score 116 may differ from a nutrient score within nutrition data 108 as target nutrient score 116 may be a nutrient score for a phenotype that a user is assigned to. Target nutrient score 116 may be generated as a function of a particular phenotype. In some embodiments, nutrient score of nutrition data 108 may be a nutrient score for a particular user that is assigned to a phenotype and target nutrient score 116 may be a nutrient score determined using data from a plurality of users sharing the same phenotype. Comparing target nutrient score to nutrition data may be a comparison between a user assigned to a phenotype and average values of all users assigned to the phenotype.

Still referring to FIG. 1, in some embodiments, apparatus 100 may be configured to generate nutrient chain. A "nutrient chain" as used in this disclosure is a set of edible items. Edible items may include, without limitation, seasonings, spices, vitamin powders, meats, seafood, fruits, vegetables, dairy products, and the like. In some embodiments, apparatus 100 may be configured to compare any data as described throughout this disclosure using an objective function. For instance, apparatus 100 may generate an objective function. An "objective function" as used in this disclosure is a process of minimizing or maximizing one or more values based on a set of constraints. In some embodiments, an objective function of apparatus 100 may include an optimization criterion. An optimization criterion may include any description of a desired value or range of values for one or more impact factors; desired value or range of values may include a maximal or minimal value, a range between maximal or minimal values, or an instruction to maximize or minimize an impact factor. As a non-limiting example, an optimization criterion may specify that an impact factor should be within a 1% difference of an optimization criterion. An optimization criterion may alternatively request that an impact factor be greater than a certain value. An optimization criterion may specify one or more tolerances for differences in macronutrients of one or more nutrients in a recipe. An optimization criterion may specify one or more desired impact factor criteria for a nutrient chain. In an embodiment, an optimization criterion may assign weights to different impact factors or values associated with impact factors. One or more weights may be expressions of value to a user of a particular outcome, impact factor value, or other facet of a nutrient chain. Optimization criteria may be combined in weighted or unweighted combinations into a function reflecting an overall outcome desired by a user; function may be a nutrient chain function to be minimized and/or maximized. A function may be defined by reference to impact factor criteria constraints and/or weighted aggregation thereof as provided by apparatus 100; for instance, an impact factor function combining optimization criteria may seek to minimize or maximize a function of nutrient chain generation.

Still referring to FIG. 1, generation of an objective function may include generation of a function to score and weight factors to achieve a process score for each feasible pairing. In some embodiments, pairings may be scored in a matrix for optimization, where columns represent nutrients and rows represent impact factors potentially paired therewith; each cell of such a matrix may represent a score of a pairing of the corresponding nutrient to the corresponding impact factor. In some embodiments, assigning a predicted process that optimizes the objective function includes performing a greedy algorithm process. A "greedy algorithm" is defined as an algorithm that selects locally optimal choices, which may or may not generate a globally optimal solution. For instance, apparatus 100 may select pairings so that scores associated therewith are the best score for each impact factor and/or for each nutrient. In such an example, optimization may determine the combination of nutrients such that each impact factor pairing includes the highest score possible.

Still referring to FIG. 1, an objective function may be formulated as a linear objective function. Apparatus 100 may solve an objective function using a linear program such as without limitation a mixed-integer program. A "linear program," as used in this disclosure, is a program that optimizes a linear objective function, given at least a constraint. For instance, and without limitation, objective function may seek to maximize a total score $\Sigma_{r \in R} \Sigma_{s \in S} c_{rs} x_{rs}$, where R is a set of all nutrients r, S is a set of all impact factors s, $c_{rs}$ is a score of a pairing of a given nutrient with a given impact factor, and $x_{rs}$ is 1 if an nutrient r is paired with an impact factor s, and 0 otherwise. Continuing the example, constraints may specify that each nutrient is assigned to only one impact factor, and each impact factor is assigned only one nutrient. Impact factors may include nutrients as described above. Sets of nutrients may be optimized for a maximum score combination of all generated nutrients. In various embodiments, apparatus 100 may determine a combination of nutrients that maximizes a total score subject to a constraint that all nutrients are paired to exactly one impact factor. Not all impact factors may receive a nutrient pairing since each impact factor may only produce one nutrient pairing. In some embodiments, an objective function may be formulated as a mixed integer optimization function. A "mixed integer optimization" as used in this disclosure is a program in which some or all of the variables are restricted to be integers. A mathematical solver may be implemented to solve for the set of feasible pairings that maximizes the sum of scores across all pairings; mathematical solver may be implemented on apparatus 100, another device, and/or may be implemented on third-party solver.

With continued reference to FIG. 1, optimizing an objective function may include minimizing a loss function, where a "loss function" is an expression an output of which an optimization algorithm minimizes to generate an optimal result. As a non-limiting example, apparatus 100 may assign variables relating to a set of parameters, which may correspond to score nutrients as described above, calculate an output of mathematical expression using the variables, and select a pairing that produces an output having the lowest size, according to a given definition of "size," of the set of outputs representing each of a plurality of nutrients and/or impact factors; size may, for instance, included absolute value, numerical size, or the like. Selection of different loss functions may result in identification of different potential pairings as generating minimal outputs. Objectives represented in an objective function and/or loss function may include minimization of impact factors. Objectives may include minimization of preparation time of a recipe. Objectives may include minimization of costs of a recipe. Objectives may include maximization of compatibility across a wide range of individuals.

Still referring to FIG. 1, optimization machine-learning model 112 may be trained using optimization training data 120. Optimization training data 120 may correlate historical nutrient data correlated to historical target nutrient scores. As used in this disclosure, "historical" is information collected over time relating to optimized meals. In some embodiments, historical data may be retrieved from a database associated with an optimization platform. In some instances, historical data may be compiled over multiple iterations of generating an optimization score, as discussed in further detail below. As a non-limiting example, training data may be stored in a training data lookup table (LUT). As used in this disclosure, a "lookup table" is an array of data that maps input values to output values. A lookup table may be used to replace a runtime computation with an array indexing operation. Optimization training data 120 may be received through user input, external computing devices, and/or previous iterations of processing. In some instances, training data may be retrieved from a database storing user data correlated to target ranges. As a non-limiting example, training data may be stored in a training data lookup table (LUT).

With continued reference to FIG. 1, target nutrient score 116 may be compared to a nutrition score included in nutrition data 108. Comparing target nutrient score 116 to nutrition score may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

With continued reference to FIG. 1, apparatus 100 may generate an optimization score 124. As used in this disclosure, "optimization score" is a measure of how accurate a score included in nutrition data is when compared to a target nutrient score. In some instances, optimization score 124 may be a numerical value based on a scale. As a non-limiting example, an optimization score 124 may be a numerical value in between 0 and 1, 0 and 10, 0 and 20, 0 and 100, or the like. IT should be noted that generating an optimization score 124 may be done over a predetermined time interval. As used in this disclosure, "predetermined time interval" is an amount of time in between two given points in time. In some instances, predetermined time interval may be a frequency of occurrence. Frequency of occurrence, as used herein, is repetition of an event after a certain amount of time has elapsed. As a non-limiting example, optimization score 124 may be generated every day, every week, every month, every quarter, every year, or the like. In some embodiments, optimization score 124 may be generated using vectors, as discussed in more detail above. In some embodiments, optimization score 124 may include a difference between target nutrient score 116 and the nutrient score of nutrition data 108, a percent difference between target nutrient score 116 and the nutrient score of nutrition data 108, an average difference between target nutrient score 116 and the nutrient score of nutrition data 108, and/or a normalized difference (such as on a scale from 0 to 1) between target nutrient score 116 and the nutrient score of nutrition data 108.

Still referring to FIG. 1, optimization score 124 may be transmitted to a graphical user interface (GUI) 128. GUI 128 may receive optimization score 124 and display optimization score 124. Optimization score 124 may be displayed as a numerical value, a graph, a chart, or the like. In some instances, optimization score 124 may change over time and said change over time may be illustrated and display on GUI 128.

Still referring to FIG. 1, optimization score 124 may be added to nutrition data 108. Apparatus 100 generating optimization score 124 and adding it to nutrition data 108 may create a feedback loop. As used in this disclosure, a "feedback loop" is a process of getting feedback relating to an output and using the feedback to as input or to modify or change future inputs to the process. As a non-limiting example, optimization score 124 may be generated every week. Optimization score 124 generated a previous week may be added to nutrition data 108. Thus, new nutrition data 108 may be input into optimization machine-learning model 112 to output target nutrient score 116. It should be noted that generating optimization score 124 by comparing target nutrient score 116 to new nutrition data may include comparing nutrient score to updated nutrition data, or any historical nutrition data. As used in this disclosure, "historical nutrition data" is nutrition information collected over time relating to optimized meals. In some embodiments, feedback received by apparatus 100 may be added to historical nutrition data such that a user may be able to access nutrition data and relevant feedback for a particular meal. Accordingly, generating an up-to-date optimization score 124 may be an iterative process. In some instances, optimization score 124 may be added to optimization training data 120. As a non-limiting example, a first optimization score may be generated and inputs input into optimization machine-learning model 112 and corresponding target nutrient scores 116 associated with the first optimization score may be added to optimization training data 120. This process may be repeated over time; creating historical training data.

Still referring to FIG. 1, a feedback loop may be created by modifying nutrition data 108 as a function of optimization score 124. As a non-limiting example, optimization score 124 may indicate that a comparison between a nutrient score included in nutrient data 108 and target nutrient score 120 may be below or above a predetermined threshold. Processor 104 may transmit a modification to nutrition data 108 in response to generating optimization score 124. In some embodiments, modifications may be a phenotype reassignment, as discussed in more detail below. As used in this disclosure, "phenotype reassignment" is classifying a user into a separate phenotype, where the separate phenotype is different than the initially assigned phenotype.

With continued reference to FIG. 1, generating optimization score 124 may cause a user to be reassigned to a different phenotype. As a non-limiting example, a user may be assigned to a first phenotype based at least on an initial data set. However, a low optimization score 124 may indicate that a user is not achieving a nutritional goal and may need to be reassigned to a phenotype that aligns more with their nutritional goals. In some embodiments, a high optimization score 124 may indicate that a user is achieving a nutritional goal and may need to readjust their phenotype group to a more difficult nutritional goal. It should be noted that reassigning a user to a separate phenotype may be done if optimization score 124 exceeds or falls below a threshold value. As a non-limiting example, a lower threshold value may be 6% and an upper threshold value may be 90%. If optimization score is 7% for a consecutive amount of predetermined time intervals, user may be reassigned to a separate phenotype. It should be noted that reassignment of a phenotype may be performed by processor 104. As a non-limiting example, processor 104 may update a phenotype of a user as a function of optimization score 124. In some instances, processor 104 may scan multiple phenotypes to extract at least a separate phenotype, from a database, which aligns better with a user's nutritional goal. It should be noted that reassignment may be performed as a function of modifying nutrition data 108. As a non-limiting example, modified nutrition data may include a nutrient score for a user, but with a nutrient score based on the separate phenotype. Accordingly, modified nutrition data input into optimization machine-learning model 112 to generate a target nutrient score for the separate phenotype and consequently, an optimization score for the separate phenotype. This process may be done until optimization score 124 is within a predetermined threshold value. In some instances, user may manually request a reassignment of phenotype group. As a non-limiting example, feedback loop may be initiated by a user using GUI 128.

With continued reference to FIG. 1, in some embodiments, apparatus 100 may be configured to generate an edible chain 132. An "edible chain" as used in this disclosure is a set of edible elements. In some cases, edible chain 132 may include a plurality of ranked edible elements 136. For the purposes of this disclosure, an "edible element" is an element of edible chain that includes nutrients that can enhance a user's health. Edible elements 136 may include, without limitation, any types of food there of, for instance, and without limitation, edible elements 136 may include spaghetti, ramen, steak, smoked salmon, salads, chips, juice, and the like. In some cases, processor 104 may be configured to generate edible chain 132 as a function of nutrition data 108 and target nutrient score 116. As a non-limiting example, processor 104 may generate edible chain 132 that includes a plurality of edible elements 136 that improving nutrient score, vibrant health score, nourishment score and meals environmental score to improving optimization score 124, which indicates that nutrition data 108 is closer to target nutrient score 116. For example, and without limitation, if a user consumes different nutrients as the user consumes edible elements 136 of edible chain 132, which provides more nutrients that the previously consuming edible elements 136, then nutrient score, vibrant health score, nourishment score and meals environmental score may improve, which will increase optimization score 124.

With continued reference to FIG. 1, in some cases, processor 104 may generate a plurality of edible elements 136 of edible chain 132 as a function of an edible quantity and nutrition data 108. For the purposes of this disclosure, an "edible quantity" is a specific amount or serving size of a particular edible element consumed. As a non-limiting example, edible quantity may include weight of edible element 136, calorie of edible element 136, or the like. In a non-limiting example, the amount of edible element 136 that a user intakes can affect the user's health. In some cases, processor 104 may generate edible element 136 as a function of biological extraction, user body measurement or physiological data of nutrition data 108. As a non-limiting example, processor 104 may generate edible chain 132 that includes edible elements 136 depending on the state of disease, types of disease, health condition of a user, or the like. In some cases, processor 104 may be configured to generate edible element 136 for edible chain 132 as a function of a consumption time interval. For the purposes of this disclosure, a "consumption time interval" is the specific times at which individuals eat their meals and snacks throughout the day. As a non-limiting example, consumption time interval may include a number of times a user consumes food or snack in a day, week, or month. For example, and without limitation, processor 104 may determine edible chain 132 that suggests consumption time interval that enhances optimization score 124 as described above.

With continued reference to FIG. 1, in some embodiments, processor 104 may be configured to rank edible elements 136 in an edible chain 132. As a non-limiting example, processor 104 may rank edible elements 136 as a function of edible quantity, consumption timing interval, preparation difficulty, preparation time, or the like. For the purposes of this disclosure, a "preparation difficulty" is the level of complexity and skill required to prepare a particular edible element. For example, and without limitation, processor 104 may rank an edible element 136 that has the maximum or high preparation difficulty to edible element 136 that has the minimum or low preparation difficulty in a descending or ascending order. For example, and without limitation, processor 104 may rank an edible element 136 that has the maximum or high preparation time to edible element 136 that has the minimum or low preparation time in a descending or ascending order. For example, and without limitation, processor 104 may rank an edible element 136 that has the maximum or high calorie content to edible element 136 that has the minimum or low calorie content in a descending or ascending order. For example, and without limitation, processor 104 may rank an edible element 136 that has the maximum or high carbohydrate, protein, fat, sodium, sugar, or the like to edible element 136 that has the minimum or low carbohydrate, protein, fat, sodium, sugar, or the like in a descending or ascending order. In some cases, processor 104 may be configured to rank edible element 136 as a function of a user input. For the purposes of this disclosure, a "user input" is any data that is inputted by a user. As a non-limiting example, a user may specify how the user wants edible element 136 to be ranked (i.e. user input). For example, and without limitation, user input may include rank request; for instance, without limitation, rank request may include a selection of protein, fat, sodium, sugar, calorie, preparation time, preparation difficulty, edible quantity, consumption timing interval, or the like. For the purposes of this disclosure, a "rank request" is a user input that inquiring the edible elements in an edible chain specifically ranked as a user wants it to be. In a non-limiting example, if a user selects 'edible quantity' through user interface, then processor 104 may rank edible elements 136 in an order to show from edible element that has maximum edible quantity to edible element that has minimum edible quantity.

With continued reference to FIG. 1, processor 104 is configured to update edible chain 132 as a function of user input received through a user interface. In some embodiments, at least a processor 104 may be further configured to generate a user interface displaying edible elements 136, edible chain 132, optimization score 124, target nutrient score 116, and the like. For the purposes of this disclosure, a "user interface" is a means by which a user and a computer system interact; for example, through the use of input devices and software. A user interface may include a graphical user interface (GUI), command line interface (CLI), menu-driven user interface, touch user interface, voice user interface (VUI), form-based user interface, any combination thereof and the like. In some embodiments, user interface may operate on and/or be communicatively connected to a decentralized platform, metaverse, and/or a decentralized exchange platform associated with the user. For example, a user may interact with user interface in virtual reality. In some embodiments, a user may interact with the use interface using a computing device distinct from and communicatively connected to processor 104. For example, a smart phone, smartwatch, tablet, or laptop operated by a user. In an embodiment, user interface may include a graphical user interface. A "graphical user interface," as used herein, is a graphical form of user interface that allows users to interact with electronic devices. In some embodiments, GUI may include icons, menus, other visual indicators or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access.

Still referring to FIG. 1, processor 104 may be configured to generate a nutrition supplement as a function of the target nutrient score. A "nutrition supplement," as used in this disclosure, is a modification or addition of the recipe of an edible element. Nutritional supplements may include, without limitation, different sets of nutrients, such as spices, seasonings, vitamin powders, drinks, and the like. In a non-limiting example, nutrition supplement may enhance nutrition score or absorption of nutrition, which may lead to an improved optimization score 124. In some embodiments, processor 104 may determine nutrition supplement as a function of nutrition data 108. As a non-limiting example, processor 104 may determine nutrition supplement based on a user's phenotype and/or randomly to optimize nutrition. In some embodiments, a nutrient classifier may be configured to receive training data correlating recipe data and/or user data to one or more nutritional supplements. Training data may be received through user, external computing devices, and/or previous iterations of processing. A nutrient classifier may receive as input nutrition data 108 and/or user data and output one or more nutritional supplements suggested by computing device that offer nutritional values aligned to target nutrient score. In some embodiments, target nutrient score 116 may be compared to nutrition data 108 when generating optimization score 124 and processor 104 may determine a nutrient deficiency. As used in this disclosure, a "nutrient deficiency" is a lack of nutrients contained in a recipe and/or meal. In some instances, a nutrient supplement may be suggested to remedy a nutrient deficiency. As a non-limiting example, optimization score 124 may indicate a user is iron deficient. Thus, processor 104 may suggest an iron supplement to a user, via GUI 128.

With continued reference to FIG. 1, in some embodiments, edible chain 132 may include a plurality of meal plans. For the purposes of this disclosure, a "meal plan" is a structured and organized set of edible elements planned for a specific period. As a non-limiting example, meal plan may include edible elements 136 for lunch, dinner, snack, or the like. In some cases, each of the plurality of meal plans may include different edible elements. As a non-limiting example, edible elements 136 for lunch may be different compared to edible elements 136 for dinner. For example, and without limitation, edible elements 136 for lunch may include higher edible quantity compared to edible elements 136 for dinner. In some cases, each of the plurality of meal plans may include differently ranked edible elements. As a non-limiting example, edible elements 136 for lunch may include edible elements that is ranked as a function of preparation difficulty while edible elements 136 for dinner may include edible elements that is ranked as a function of calorie.

With continued reference to FIG. 1, in some cases, processor 104 may be configured to generate edible chain 132 using a machine-learning module. Machine-learning module disclosed herein is further described with respect to FIG. 2. In some cases, processor 104 may be configured to generate chain training data. As a non-limiting example, chain training data may include correlations between exemplary nutrition data, exemplary target nutrient scores, and exemplary edible chains. As another non-limiting example, chain training data may include correlations between exemplary edible quantities, exemplary consumption time intervals, exemplary food chains, exemplary meal plans, or the like. In some embodiments, chain training data may be stored in database. In some embodiments, chain training data may be received from one or more users, database, external computing devices, and/or previous iterations of processing. As a non-limiting example, chain training data may include instructions from a user, who may be an expert user, a past user in embodiments disclosed herein, or the like, which may be stored in memory and/or stored in database, where the instructions may include labeling of training examples. In some embodiments, chain training data may be updated iteratively on a feedback loop. As a non-limiting example, processor 104 may update chain training data iteratively on a feedback loop as a function of newly collected nutrition data 108, target nutrient score 116, optimization score 124, edible chain 132, input and/or output of optimization model 112, user input, or the like. In some embodiments, processor 104 may be configured to generate chain machine-learning model 140. In a non-limiting example, generating chain machine-learning model 140 may include training, retraining, or fine-tuning chain machine-learning model 140 using chain training data or updated chain training data. In some embodiments, processor 104 may be configured to determine edible chain 132 using chain machine-learning model 140 (i.e. trained or updated chain machine-learning model 140). In some embodiments, generating training data and training machine-learning models may be simultaneous.

With continued reference to FIG. 1, in some embodiments, apparatus 100 may be configured to compare any data as described throughout this disclosure using an objective function. For instance, apparatus 100 may generate an objective function. An "objective function" as used in this disclosure is a process of minimizing or maximizing one or more values based on a set of constraints. In some embodiments, an objective function of apparatus 100 may include an optimization criterion. An optimization criterion may include any description of a desired value or range of values for one or more impact factors; desired value or range of values may include a maximal or minimal value, a range between maximal or minimal values, or an instruction to maximize or minimize an impact factor. As a non-limiting example, an optimization criterion may specify that an impact factor should be within a 1% difference of an optimization criterion. An optimization criterion may alternatively request that an impact factor be greater than a certain value. An optimization criterion may specify one or more tolerances for differences in macronutrients of one or more nutrients in a recipe. An optimization criterion may specify one or more desired impact factor criteria for edible chain 132. In an embodiment, an optimization criterion may assign weights to different impact factors or values associated with impact factors. One or more weights may be expressions of value to a user of a particular outcome, impact factor value, or other facet of edible chain 132. Optimization criteria may be combined in weighted or unweighted combinations into a function reflecting an overall outcome desired by a user; function may be edible chain 132 function to be minimized and/or maximized. A function may be defined by reference to impact factor criteria constraints and/or weighted aggregation thereof as provided by apparatus 100; for instance, an impact factor function combining optimization criteria may seek to minimize or maximize a function of edible chain 132 generation.

Still referring to FIG. 1, generation of an objective function may include generation of a function to score and weight factors to achieve a process score for each feasible pairing. In some embodiments, pairings may be scored in a matrix for optimization, where columns represent nutrients and rows represent impact factors potentially paired therewith; each cell of such a matrix may represent a score of a pairing of the corresponding nutrient to the corresponding impact factor. In some embodiments, assigning a predicted process that optimizes the objective function includes performing a greedy algorithm process. A "greedy algorithm" is defined as an algorithm that selects locally optimal choices, which may or may not generate a globally optimal solution. For instance, apparatus 100 may select pairings so that scores associated therewith are the best score for each impact factor and/or for each nutrient. In such an example, optimization may determine the combination of nutrients such that each impact factor pairing includes the highest score possible.

Still referring to FIG. 1, an objective function may be formulated as a linear objective function. Apparatus 100 may solve an objective function using a linear program such as without limitation a mixed-integer program. A "linear program," as used in this disclosure, is a program that optimizes a linear objective function, given at least a constraint. For instance, and without limitation, objective function may seek to maximize a total score $\Sigma_{r \in R} \Sigma_{s \in S} c_{rs} x_{rs}$, where R is a set of all nutrients r, S is a set of all impact factors s, $c_{rs}$ is a score of a pairing of a given nutrient with a given impact factor, and $x_{rs}$ is 1 if an nutrient r is paired with an impact factor s, and 0 otherwise. Continuing the example, constraints may specify that each nutrient is assigned to only one impact factor, and each impact factor is assigned only one nutrient. Impact factors may include nutrients as described above. Sets of nutrients may be optimized for a maximum score combination of all generated nutrients. In various embodiments, apparatus 100 may determine a combination of nutrients that maximizes a total score subject to a constraint that all nutrients are paired to exactly one impact factor. Not all impact factors may receive a nutrient pairing since each impact factor may only produce one nutrient pairing. In some embodiments, an objective function may be formulated as a mixed integer optimization function. A "mixed integer optimization" as used in this disclosure is a program in which some or all of the variables are restricted to be integers. A mathematical solver may be implemented to solve for the set of feasible pairings that maximizes the sum of scores across all pairings; mathematical solver may be implemented on apparatus 100, another device, and/or may be implemented on third-party solver.

With continued reference to FIG. 1, optimizing an objective function may include minimizing a loss function, where a "loss function" is an expression an output of which an optimization algorithm minimizes to generate an optimal result. As a non-limiting example, apparatus 100 may assign variables relating to a set of parameters, which may correspond to score nutrients as described above, calculate an output of mathematical expression using the variables, and select a pairing that produces an output having the lowest size, according to a given definition of "size," of the set of outputs representing each of a plurality of nutrients and/or impact factors; size may, for instance, included absolute value, numerical size, or the like. Selection of different loss functions may result in identification of different potential pairings as generating minimal outputs. Objectives represented in an objective function and/or loss function may include minimization of impact factors. Objectives may include minimization of preparation time of a recipe. Objectives may include minimization of costs of a recipe. Objectives may include maximization of compatibility across a wide range of individuals.

With continued reference to FIG. 1, in some embodiments, generate an edible data structure for edible chain 132 using a large language model. For the purposes of this disclosure, an "edible data structure" is a structured organization of data related to an edible chain. In some embodiments, edible data structure may provide a summarization, representation, or otherwise abstraction of edible chain 132. In a non-limiting example, edible data structure may include a comprehensive report on edible chain 132. In another non-limiting example, edible data structure may include short explanations detailing reasoning behind ranked edible elements 136 in edible chain 132. In some embodiments, edible data structure may include a form of text, graph, trend line, chart, audio, animation, image, video, and the like. In some embodiments, edible data structure may include text, images, tables, charts, graphs, or other elements. In some embodiments, edible data structure may include various format. As a non-limiting example, edible data structure may include PDF, DOC, XLS, HTML, PNC, JPEG, BMP, TIFF, MP4, or the like. In an embodiment, edible data structure may include a hard copy form. In another embodiment, edible data structure may include an electronic copy form. In some embodiments, a user may manually generate edible data structure or processor 104 may generate edible data structure through the use of machine-learning module.

With continued reference to FIG. 1, large language model may be a type of generative AI. A "large language model," as used herein, is a deep learning algorithm that can recognize, summarize, translate, predict and/or generate text and other content based on knowledge gained from massive datasets. LLMs may be trained on large sets of data; for example, training sets may include greater than 1 million words. Training sets may be drawn from diverse sets of data such as, as non-limiting examples, novels, blog posts, articles, emails, and the like. Training sets may include a variety of subject matters, such as, as nonlimiting examples, medical tests, romantic ballads, beat poetry, emails, advertising documents, newspaper articles, and the like. LLMs, in some embodiments, may include GPT, GPT-2, GPT-3, and other language processing models. LLM may be used to augment the text in an article based on a prompt. Training data may correlate elements of a dictionary related to linguistics, as described above, to a prompt. LLM may include a text prediction based algorithm configured to receive an article and apply a probability distribution to the words already typed in a sentence to work out the most likely word to come next in augmented articles. For example, if the words already typed are "Nice to meet," then it is highly likely that the word "you" will come next. LLM may output such predictions by ranking words by likelihood or a prompt parameter. For the example given above, the LLM may score "you" as the most likely, "your" as the next most likely, "his" or "her" next, and the like.

With reference to FIG. 1, LLM may include an attention mechanism, utilizing a transformer as described further below. An "attention mechanism," as used herein, is a part of a neural architecture that enables a system to dynamically highlight relevant features of the input data. In natural language processing this may be a sequence of textual elements. It may be applied directly to the raw input or to its higher-level representation. An attention mechanism may be an improvement to the limitation of the Encoder-Decoder model which encodes the input sequence to one fixed length vector from which to decode the output at each time step. This issue may be seen as a problem when decoding long sequences because it may make it difficult for the neural network to cope with long sentences, such as those that are longer than the sentences in the training corpus. Applying an attention mechanism, LLM may predict the next word by searching for a set of position in a source sentence where the most relevant information is concentrated. LLM may then predict the next word based on context vectors associated with these source positions and all the previously generated target words, such as textual data of a dictionary correlated to a prompt in a training data set. A "context vector," as used herein, are fixed-length vector representations useful for document retrieval and word sense disambiguation. In some embodiments, LLM may include encoder-decoder model incorporating an attention mechanism.

With reference to FIG. 1, LLM may include a transformer architecture. In some embodiments, encoder component of LLM may include transformer architecture. A "transformer architecture," for the purposes of this disclosure is a neural network architecture that uses self-attention and positional encoding. Transformer architecture may be designed to process sequential input data, such as natural language, with applications towards tasks such as translation and text summarization. Transformer architecture may process the entire input all at once. "Positional encoding," for the purposes of this disclosure, refers to a data processing technique that encodes the location or position of an entity in a sequence. In some embodiments, each position in the sequence may be assigned a unique representation. In some embodiments, positional encoding may include mapping each position in the sequence to a position vector. In some embodiments, trigonometric functions, such as sine and cosine, may be used to determine the values in the position vector. In some embodiments, position vectors for a plurality of positions in a sequence may be assembled into a position matrix, wherein each row of position matrix may represent a position in the sequence.

With continued reference to FIG. 1, an attention mechanism may represent an improvement over a limitation of the Encoder-Decoder model. The encoder-decider model encodes the input sequence to one fixed length vector from which the output is decoded at each time step. This issue may be seen as a problem when decoding long sequences because it may make it difficult for the neural network to cope with long sentences, such as those that are longer than the sentences in the training corpus. Applying an attention mechanism, LLM may predict the next word by searching for a set of positions in a source sentence where the most relevant information is concentrated. LLM may then predict the next word based on context vectors associated with these source positions and all the previously generated target words, such as textual data of a dictionary correlated to a prompt in a training data set. A "context vector," as used herein, are fixed-length vector representations useful for document retrieval and word sense disambiguation.

With reference to FIG. 1, an attention mechanism may include generalized attention self-attention, multi-head attention, additive attention, global attention, and the like. In generalized attention, when a sequence of words or an image is fed to LLM, it may verify each element of the input sequence and compare it against the output sequence. Each iteration may involve the mechanism's encoder capturing the input sequence and comparing it with each element of the decoder's sequence. From the comparison scores, the mechanism may then select the words or parts of the image that it needs to pay attention to. In self-attention, LLM may pick up particular parts at different positions in the input sequence and over time compute an initial composition of the output sequence. In multi-head attention, LLM may include a transformer model of an attention mechanism. Attention mechanisms, as described above, may provide context for any position in the input sequence. For example, if the input data is a natural language sentence, the transformer does not have to process one word at a time. In multi-head attention, computations by LLM may be repeated over several iterations, each computation may form parallel layers known as attention heads. Each separate head may independently pass the input sequence and corresponding output sequence element through a separate head. A final attention score may be produced by combining attention scores at each head so that every nuance of the input sequence is taken into consideration. In additive attention (Bahdanau attention mechanism), LLM may make use of attention alignment scores based on a number of factors. These alignment scores may be calculated at different points in a neural network. Source or input sequence words are correlated with target or output sequence words but not to an exact degree. This correlation may take into account all hidden states and the final alignment score is the summation of the matrix of alignment scores. In global attention (Luong mechanism), in situations where neural machine translations are required, LLM may either attend to all source words or predict the target sentence, thereby attending to a smaller subset of words.

With continued reference to FIG. 1, multi-headed attention in encoder may apply a specific attention mechanism called self-attention. Self-attention allows the models to associate each word in the input, to other words. So, as a non-limiting example, the LLM may learn to associate the word "you," with "how" and "are." It's also possible that LLM learns that words structured in this pattern are typically a question and to respond appropriately. In some embodiments, to achieve self-attention, input may be fed into three distinct fully connected layers to create query, key, and value vectors. The query, key, and value vectors may be fed through a linear layer; then, the query and key vectors may be multiplied using dot product matrix multiplication in order to produce a score matrix. The score matrix may determine the amount of focus for a word should be put on other words (thus, each word may be a score that corresponds to other words in the time-step). The values in score matrix may be scaled down. As a non-limiting example, score matrix may be divided by the square root of the dimension of the query and key vectors. In some embodiments, the softmax of the scaled scores in score matrix may be taken. The output of this softmax function may be called the attention weights. Attention weights may be multiplied by your value vector to obtain an output vector. The output vector may then be fed through a final linear layer.

With continued reference to FIG. 1, in order to use self-attention in a multi-headed attention computation, query, key, and value may be split into N vectors before applying self-attention. Each self-attention process may be called a "head." Each head may produce an output vector and each output vector from each head may be concatenated into a single vector. This single vector may then be fed through the final linear layer discussed above. In theory, each head can learn something different from the input, therefore giving the encoder model more representation power.

With continued reference to FIG. 1, encoder of transformer may include a residual connection. Residual connection may include adding the output from multi-headed attention to the positional input embedding. In some embodiments, the output from residual connection may go through a layer normalization. In some embodiments, the normalized residual output may be projected through a pointwise feed-forward network for further processing. The pointwise feed-forward network may include a couple of linear layers with a ReLU activation in between. The output may then be added to the input of the pointwise feed-forward network and further normalized.

With continued reference to FIG. 1, transformer architecture may include a decoder. Decoder may a multi-headed attention layer, a pointwise feed-forward layer, one or more residual connections, and layer normalization (particularly after each sub-layer), as discussed in more detail above. In some embodiments, decoder may include two multi-headed attention layers. In some embodiments, decoder may be autoregressive. For the purposes of this disclosure, "autoregressive" means that the decoder takes in a list of previous outputs as inputs along with encoder outputs containing attention information from the input.

With continued reference to FIG. 1, in some embodiments, input to decoder may go through an embedding layer and positional encoding layer in order to obtain positional embeddings. Decoder may include a first multi-headed attention layer, wherein the first multi-headed attention layer may receive positional embeddings.

With continued reference to FIG. 1, first multi-headed attention layer may be configured to not condition to future tokens. As a non-limiting example, when computing attention scores on the word "am," decoder should not have access to the word "fine" in "I am fine," because that word is a future word that was generated after. The word "am" should only have access to itself and the words before it. In some embodiments, this may be accomplished by implementing a look-ahead mask. Look ahead mask is a matrix of the same dimensions as the scaled attention score matrix that is filled with "0s" and negative infinities. For example, the top right triangle portion of look-ahead mask may be filed with negative infinities. Look-ahead mask may be added to scaled attention score matrix to obtain a masked score matrix. Masked score matrix may include scaled attention scores in the lower-left triangle of the matrix and negative infinities in the upper-right triangle of the matrix. Then, when the SoftMax of this matrix is taken, the negative infinities will be zeroed out; this leaves "zero" attention scores for "future tokens."

With continued reference to FIG. 1, second multi-headed attention layer may use encoder outputs as queries and keys and the outputs from the first multi-headed attention layer as values. This process matches the encoder's input to the decoder's input, allowing the decoder to decide which encoder input is relevant to put a focus on. The output from second multi-headed attention layer may be fed through a pointwise feedforward layer for further processing.

With continued reference to FIG. 1, the output of the pointwise feedforward layer may be fed through a final linear layer. This final linear layer may act as a classifier. This classifier may be as big as the number of classes that you have. For example, if you have 10,000 classes for 10,000 words, the output of that classes will be of size 10,000. The output of this classifier may be fed into a SoftMax layer which may serve to produce probability scores between zero and one. The index may be taken of the highest probability score in order to determine a predicted word.

With continued reference to FIG. 1, decoder may take this output and add it to the decoder inputs. Decoder may continue decoding until a token is predicted. Decoder may stop decoding once it predicts an end token. In some embodiment, decoder may be stacked N layers high, with each layer taking in inputs from the encoder and layers before it. Stacking layers may allow LLM to learn to extract and focus on different combinations of attention from its attention heads.

With continued reference to FIG. 1, in some embodiments, LLM may be specifically trained using large language model (LLM) training data. In some embodiments, LLM training data may include correlations between exemplary nutrition data, exemplary edible chains, exemplary nutrient target scores, exemplary optimization scores 124, exemplary edible data structures, or the like. As a non-limiting example, LLM training data may include correlations between phenotypes, physiological data, edible elements 136 of edible chain 132 and edible data structure. In some embodiments, LLM training data may include a set of data that is in user's voice, email, or the like to mimic them. In some embodiments, LLM training data may be consistent with any training data described in the entirety of this disclosure. In some embodiments, LLM training data may be received from one or more users, database, external computing devices, and/or previous iterations of processing. As a non-limiting example, LLM training data may include instructions from a user, who may be an expert user, a past user in embodiments disclosed herein, or the like, which may be stored in memory and/or stored in database, where the instructions may include labeling of training examples. In some embodiments, LLM training data may be updated iteratively on a feedback loop. As a non-limiting example, LLM training data may be updated iteratively on a feedback loop as a function of newly collected nutrition data 108, target nutrient score 116, optimization score 124, edible chain 132, input and/or output of machine-learning module, such as but not limited to optimization machine-learning model 112, chain machine-learning model 140, or the like. In some embodiments, processor 104 may be configured to generate LLM. In a non-limiting example, generating LLM may include training, retraining, or fine-tuning LLM using LLM training data or updated LLM training data. In some embodiments, processor 104 may be configured to generate edible data structure using LLM (i.e. trained or updated LLM).

Figure 2:
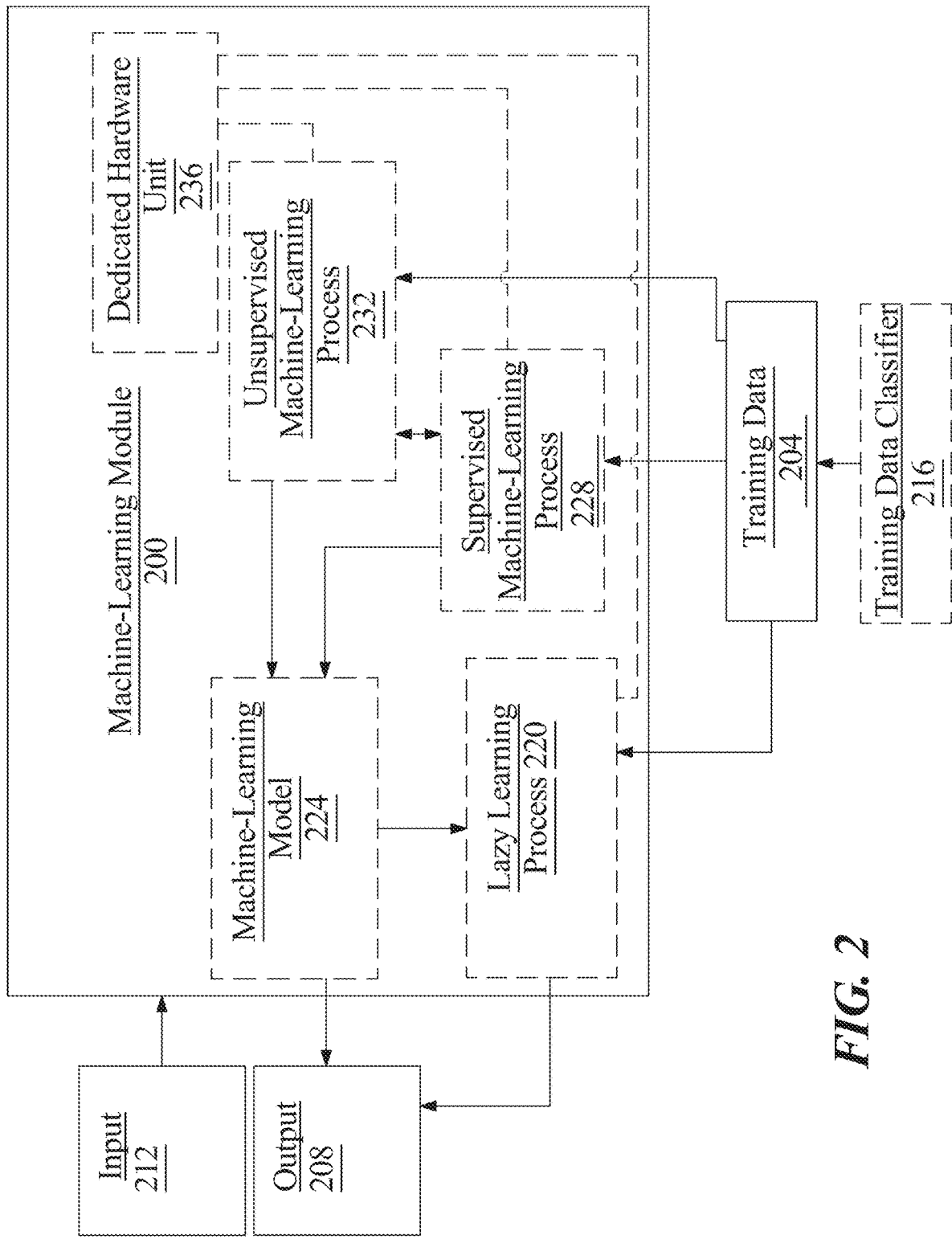
FIG. 2 illustrates a block diagram of an exemplary embodiment of a machine-learning model.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine-learning processes. A "machine-learning process," as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine-learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative input data may include nutrition data 108, input or output of any machine-learning models of machine-learning module described herein. As a non-limiting illustrative output data may include optimization score 124, edible chain 132, input or output of any machine-learning models of machine-learning module described herein.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine-learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to a cohort of user. For example, and without limitation, training data classifier 216 may classify elements of training data to a type of phenotype, gender, occupation, location, or the like.

Still referring to FIG. 2, computing device 204 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)÷P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 204 may then calculate a likelihood table by calculating probabilities of different data entries and classification labels. Computing device 204 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 2, computing device 204 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 2, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 2, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 2, computer, processor, and/or module may be configured to preprocess training data. "Preprocessing" training data, as used in this disclosure, is transforming training data from raw form to a format that can be used for training a machine-learning model. Preprocessing may include sanitizing, feature selection, feature scaling, data augmentation and the like.

Still referring to FIG. 2, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor, and/or module may be configured to precondition one or more training examples. For instance, and without limitation, where a machine-learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine-learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine-learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 2, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 2, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 2, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}: X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 2, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine-learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include nutrition data 108, input or output of any machine-learning models of machine-learning module as input and optimization score 124, edible chain 132, input or output of any machine-learning models of machine-learning module as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 2, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine-learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 232 may not require a response variable; unsupervised processes 232 may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 236. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 236 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 236 may include, without limitation, graphical processing units (GPUs), dedicated signal processing modules, FPGA or other reconfigurable hardware that has been configured to instantiate parallel processing units for one or more specific tasks, or the like. A computing device, processor, apparatus, or module may be configured to instruct one or more dedicated hardware units 236 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 3:
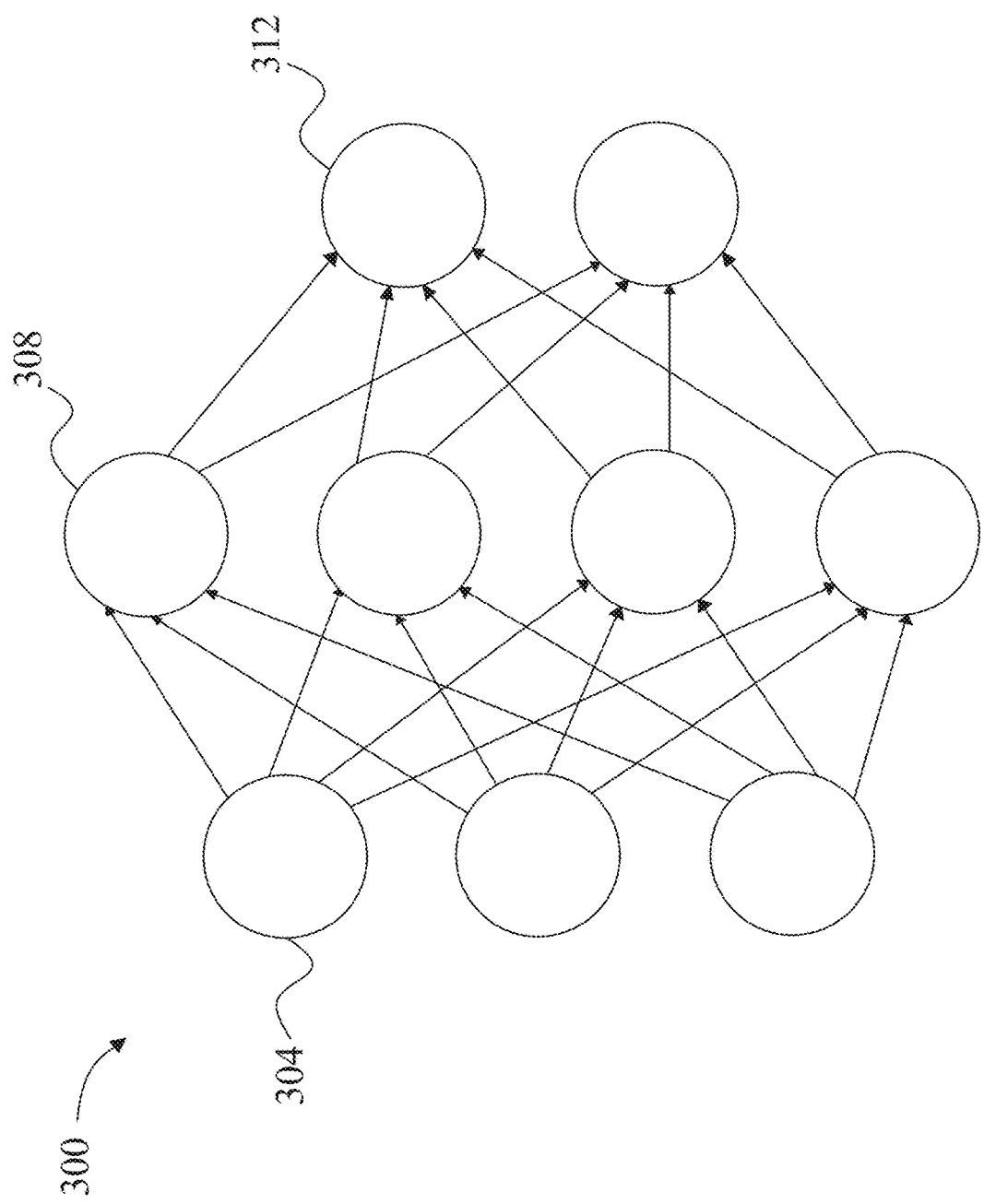
FIG. 3 illustrates a diagram of an exemplary embodiment of a neural network.

Referring now to FIG. 3, an exemplary embodiment of neural network 300 is illustrated. A neural network 300 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 304, one or more intermediate layers 308, and an output layer of nodes 312. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 4:
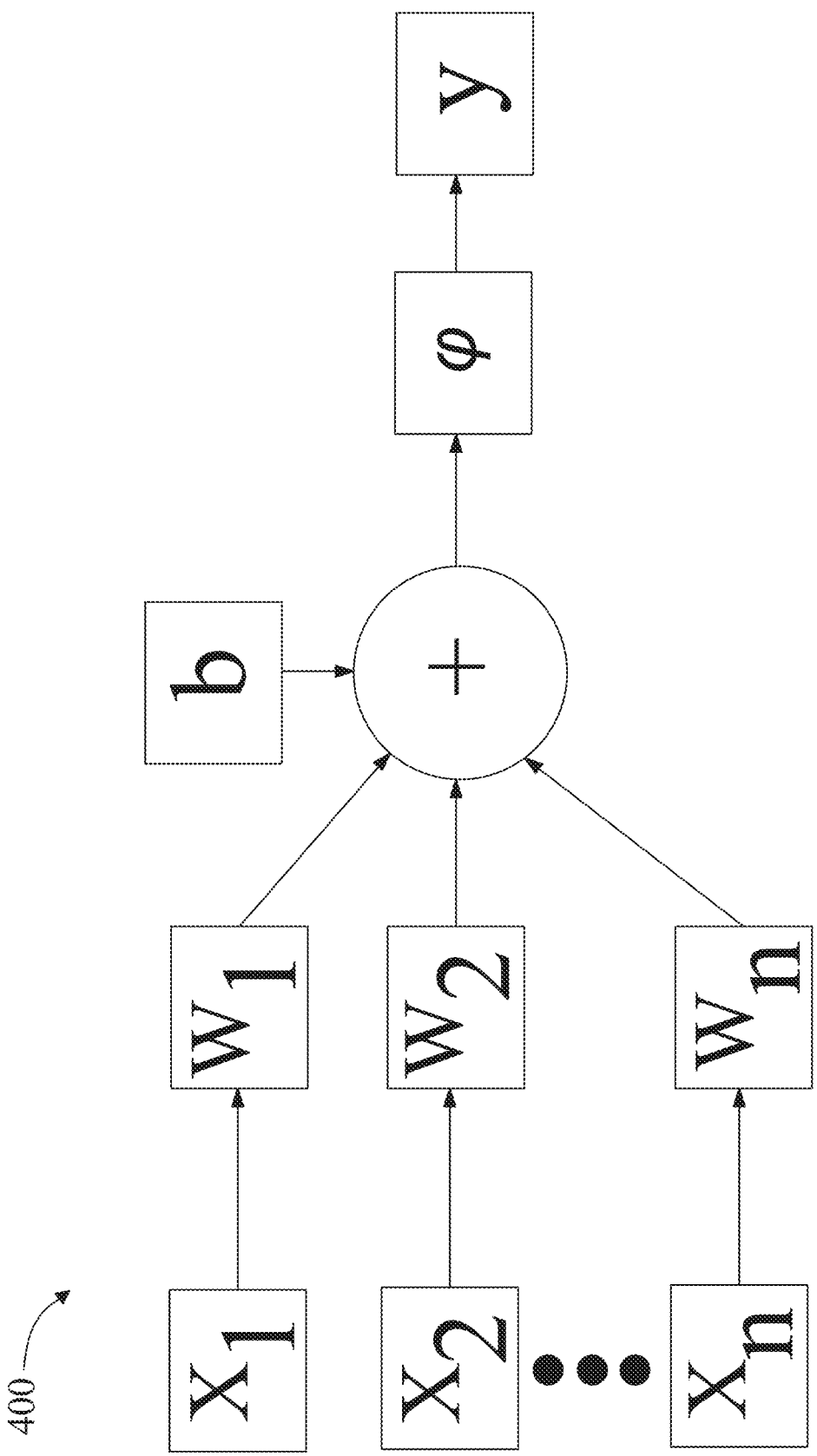
FIG. 4 illustrates a diagram of an exemplary embodiment of a node of a neural network.

Referring now to FIG. 4, an exemplary embodiment of a node 400 of a neural network is illustrated. A node may include, without limitation, a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 5:
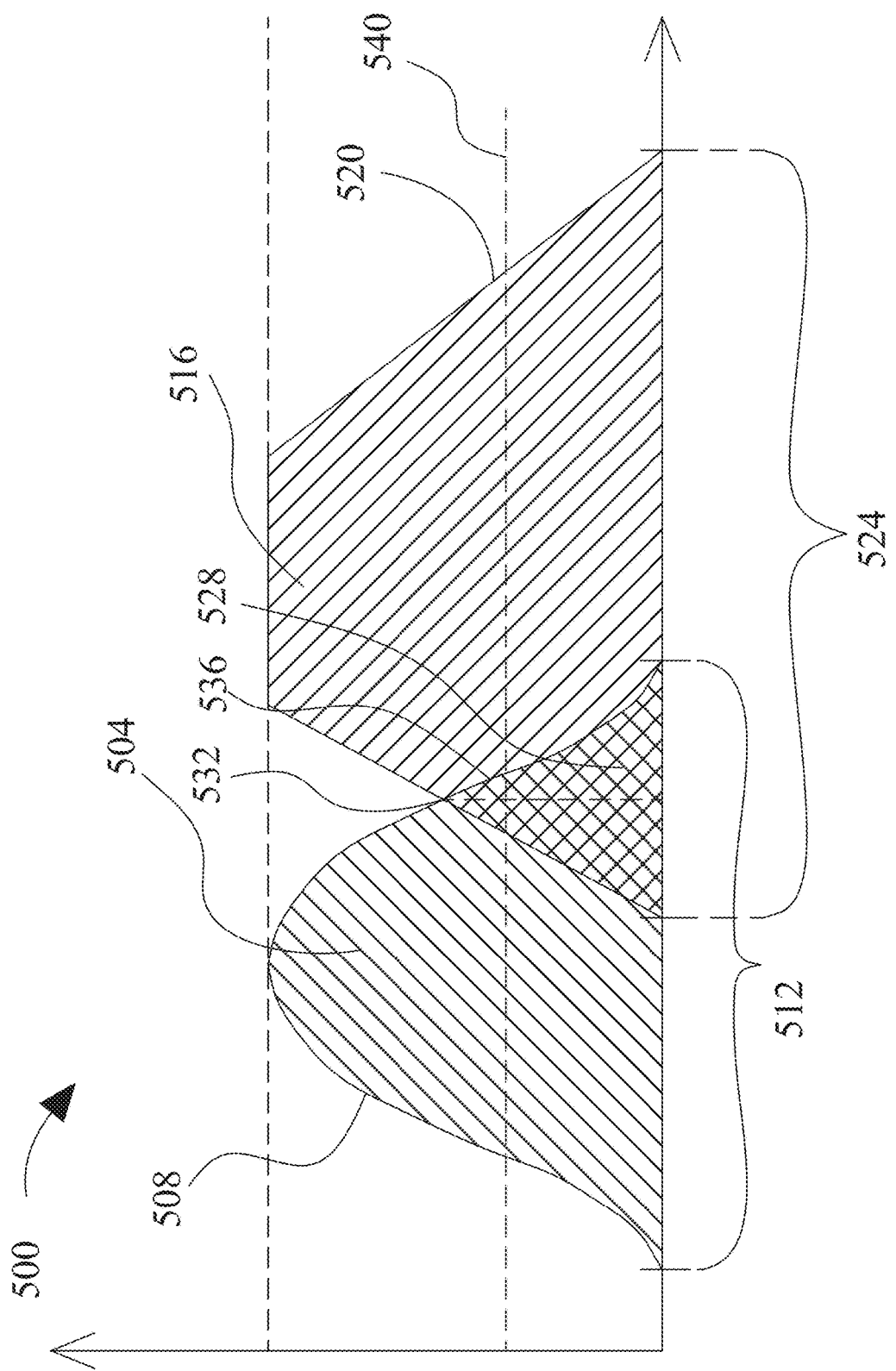
FIG. 5 illustrates a graph illustrating an exemplary relationship between fuzzy sets.

Referring to FIG. 5, an exemplary embodiment of fuzzy set comparison 500 is illustrated. A first fuzzy set 504 may be represented, without limitation, according to a first membership function 508 representing a probability that an input falling on a first range of values 512 is a member of the first fuzzy set 504, where the first membership function 508 has values on a range of probabilities such as without limitation the interval [0,1], and an area beneath the first membership function 508 may represent a set of values within first fuzzy set 504. Although first range of values 512 is illustrated for clarity in this exemplary depiction as a range on a single number line or axis, first range of values 512 may be defined on two or more dimensions, representing, for instance, a Cartesian product between a plurality of ranges, curves, axes, spaces, dimensions, or the like. First membership function 508 may include any suitable function mapping first range 512 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, & \text{for } x > c \text{ and } x < a \\ \frac{x-a}{b-a}, & \text{for } a \le x < b \\ \frac{c-x}{c-b}, & \text{if } b < x \le c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}(\frac{x-c}{\sigma})^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 5, first fuzzy set 504 may represent any value or combination of values as described above, including output from one or more machine-learning models, nutrition data, target nutrient scores, and a predetermined class, such as without limitation of nutrient sufficient, nutrient deficient, or the like. A second fuzzy set 516, which may represent any value which may be represented by first fuzzy set 504, may be defined by a second membership function 520 on a second range 524; second range 524 may be identical and/or overlap with first range 512 and/or may be combined with first range via Cartesian product or the like to generate a mapping permitting evaluation overlap of first fuzzy set 504 and second fuzzy set 516. Where first fuzzy set 504 and second fuzzy set 516 have a region 528 that overlaps, first membership function 508 and second membership function 520 may intersect at a point 532 representing a probability, as defined on probability interval, of a match between first fuzzy set 504 and second fuzzy set 516. Alternatively or additionally, a single value of first and/or second fuzzy set may be located at a locus 536 on first range 512 and/or second range 524, where a probability of membership may be taken by evaluation of first membership function 508 and/or second membership function 520 at that range point. A probability at 528 and/or 532 may be compared to a threshold 540 to determine whether a positive match is indicated. Threshold 540 may, in a non-limiting example, represent a degree of match between first fuzzy set 504 and second fuzzy set 516, and/or single values therein with each other or with either set, which is sufficient for purposes of the matching process; for instance, threshold may indicate a sufficient degree of overlap between an output from one or more machine-learning models and/or nutrition data, target nutrient scores and a predetermined class, such as without limitation nutrient performance categorization, for combination to occur as described above. Alternatively or additionally, each threshold may be tuned by a machine-learning and/or statistical process, for instance and without limitation as described in further detail below.

Further referring to FIG. 5, in an embodiment, a degree of match between fuzzy sets may be used to classify a nutrition data, target nutrient scores with nutrient performance. For instance, if a nutrient performance has a fuzzy set matching nutrition data, target nutrient scores fuzzy set by having a degree of overlap exceeding a threshold, processor 104 may classify the nutrition data, target nutrient scores as belonging to the nutrient sufficient categorization. Where multiple fuzzy matches are performed, degrees of match for each respective fuzzy set may be computed and aggregated through, for instance, addition, averaging, or the like, to determine an overall degree of match.

Still referring to FIG. 5, in an embodiment, nutrition data, target nutrient scores may be compared to multiple nutrient performance categorization fuzzy sets. For instance, nutrition data, target nutrient scores may be represented by a fuzzy set that is compared to each of the multiple nutrient performance categorization fuzzy sets; and a degree of overlap exceeding a threshold between the nutrition data, target nutrient scores fuzzy set and any of the multiple nutrient performance categorization fuzzy sets may cause processor 104 to classify the nutrition data, target nutrient scores as belonging to nutrient sufficient categorization. For instance, in one embodiment there may be two nutrient sufficiency categorization fuzzy sets, representing respectively nutrient sufficient categorization and a nutrient deficient categorization. First nutrient sufficiency categorization may have a first fuzzy set; Second nutrient performance categorization may have a second fuzzy set; and nutrition data, target nutrient scores may have nutrition data, target nutrient scores fuzzy set. Processor 104, for example, may compare nutrition data, target nutrient scores fuzzy set with each of nutrient performance categorization fuzzy set and in nutrient performance categorization fuzzy set, as described above, and classify a nutrition data, target nutrient scores to either, both, or neither of nutrient performance categorization or in nutrient performance categorization. Machine-learning methods as described throughout may, in a non-limiting example, generate coefficients used in fuzzy set equations as described above, such as without limitation x, c, and a of a Gaussian set as described above, as outputs of machine-learning methods. Likewise, nutrition data, target nutrient scores may be used indirectly to determine a fuzzy set, as nutrition data, target nutrient scores fuzzy set may be derived from outputs of one or more machine-learning models that take the nutrition data, target nutrient scores directly or indirectly as inputs.

Still referring to FIG. 5, a computing device may use a logic comparison program, such as, but not limited to, a fuzzy logic model to determine a nutrient performance response. An nutrient performance response may include, but is not limited to, sufficient, deficient, and the like; each such nutrient performance response may be represented as a value for a linguistic variable representing nutrient performance response or in other words a fuzzy set as described above that corresponds to a degree of performance as calculated using any statistical, machine-learning, or other method that may occur to a person skilled in the art upon reviewing the entirety of this disclosure. In some embodiments, determining a nutrient performance categorization may include using a linear regression model. A linear regression model may include a machine-learning model. A linear regression model may be configured to map data of nutrition data, target nutrient scores, such as degree of . . . to one or more nutrient performance parameters. A linear regression model may be trained using a machine-learning process. A linear regression model may map statistics such as, but not limited to, quality of nutrition data, target nutrient scores or the like. In some embodiments, determining a nutrient performance of nutrition data, target nutrient scores may include using a nutrient performance classification model. A nutrient performance classification model may be configured to input collected data and cluster data to a centroid based on, but not limited to, frequency of appearance, linguistic indicators of quality, and the like. Centroids may include scores assigned to them such that quality of nutrition data, target nutrient scores may each be assigned a score. In some embodiments nutrient performance classification model may include a K-means clustering model. In some embodiments, nutrient performance classification model may include a particle swarm optimization model. In some embodiments, determining the nutrient performance of nutrition data, target nutrient scores may include using a fuzzy inference engine. A fuzzy inference engine may be configured to map one or more nutrition data, target nutrient scores data elements using fuzzy logic. In some embodiments, nutrition data, target nutrient scores may be arranged by a logic comparison program into nutrient performance arrangement. An "nutrient performance arrangement" as used in this disclosure is any grouping of objects and/or data based on skill level and/or output score. This step may be implemented as described above in FIGS. 1-4. Membership function coefficients and/or constants as described above may be tuned according to classification and/or clustering algorithms. For instance, and without limitation, a clustering algorithm may determine a Gaussian or other distribution of questions about a centroid corresponding to a given performance level, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Further referring to FIG. 5, an inference engine may be implemented according to input and/or output membership functions and/or linguistic variables. For instance, a first linguistic variable may represent a first measurable value pertaining to nutrition data, target nutrient scores, such as a degree of performance of an element, while a second membership function may indicate a degree of in nutrient performance of a subject thereof, or another measurable value pertaining to nutrition data, target nutrient scores. Continuing the example, an output linguistic variable may represent, without limitation, a score value. An inference engine may combine rules, such as: "if the performance level is "sufficient," the question score is 'high'"—the degree to which a given input function membership matches a given rule may be determined by a triangular norm or "T-norm" of the rule or output membership function with the input membership function, such as min (a, b), product of a and b, drastic product of a and b, Hamacher product of a and b, or the like, satisfying the rules of commutativity ($T(a, b)=T(b, a)$), monotonicity: ($T(a, b) \leq T(c, d)$ if $a \leq c$ and $b \leq d$), (associativity: $T(a, T(b, c))=T(T(a, b), c)$), and the requirement that the number 1 acts as an identity element. Combinations of rules ("and" or "or" combination of rule membership determinations) may be performed using any T-conorm, as represented by an inverted T symbol or "⊥," such as max(a, b), probabilistic sum of a and b (a+b−a*b), bounded sum, and/or drastic T-conorm; any T-conorm may be used that satisfies the properties of commutativity: $\bot(a, b)=\bot(b, a)$, monotonicity: $\bot(a, b) \leq \bot(c, d)$ if $a \leq c$ and $b \leq d$, associativity: $\bot(a, \bot(b, c))=\bot(\bot(a, b), c)$, and identity element of 0. Alternatively or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively or additionally, output rules may be replaced with functions according to the Takagi-Sugeno-King (TSK) fuzzy model.

Figure 6:
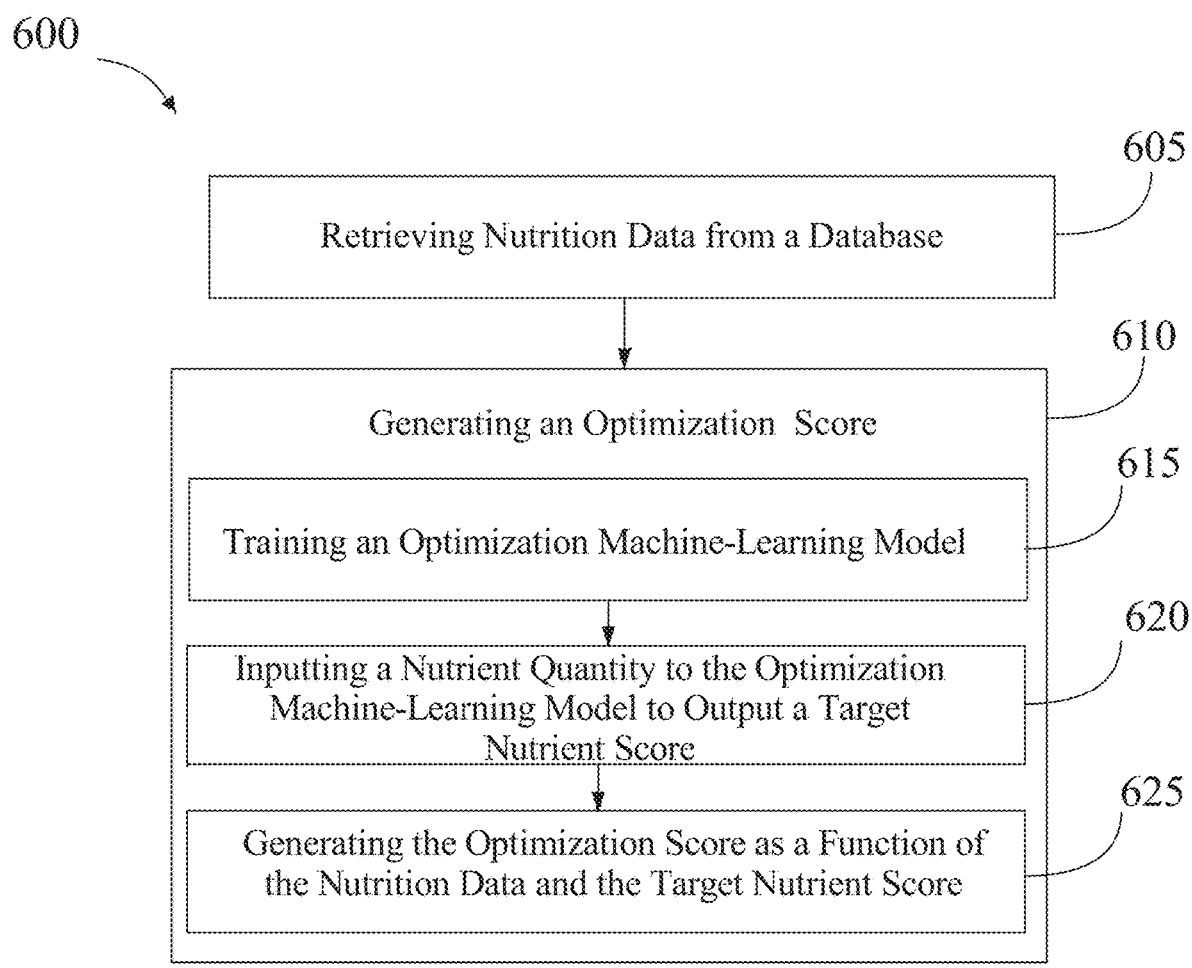
FIG. 6 illustrates a flowchart of an exemplary for using a feedback loop to optimize meals.

Referring now to FIG. 6, a method 600 for using a feedback loop to optimize meals. At step 605, method 600 may include retrieving, by processor, nutrition data from a database. Nutrition data may include at least a nutrient score. Nutrition data may include nutrient data. Nutrition data may be a function of a geofenced area, where the geofenced area is a geographical area. This step may be implemented as described above with reference to FIGS. 1-2, without limitation.

Still referring to FIG. 6, at step 610, method 600 may include generating, by the processor, an optimization score. This step may be implemented as described above with reference to FIGS. 1-5, without limitation.

Still referring to FIG. 6, at step 615, generating the optimization score may include training an optimization machine-learning model with optimization training data. In some embodiments, training data may include comprises historical nutrition data correlated to historical target nutrient scores. This step may be implemented as described above with reference to FIGS. 1-5, without limitation.

Still referring to FIG. 6, at step 620, generating the optimization score may include inputting a nutrient quantity to the optimization machine-learning model to output a target nutrient score. This step may be implemented as described above with reference to FIGS. 1-5, without limitation.

Still referring to FIG. 6, at step 625, optimization score may be generated as a function of nutrition data and the target nutrient score. In some embodiments, generating the optimization score comprises comparing the nutrition data to the target nutrient score. In some embodiments, generating the optimization score may include a plurality of iterations over a predetermined time interval. In some embodiments, generating the optimization score may update a phenotype group assignment for a user. This step may be implemented as described above with reference to FIGS. 1-5, without limitation.

Figure 7:
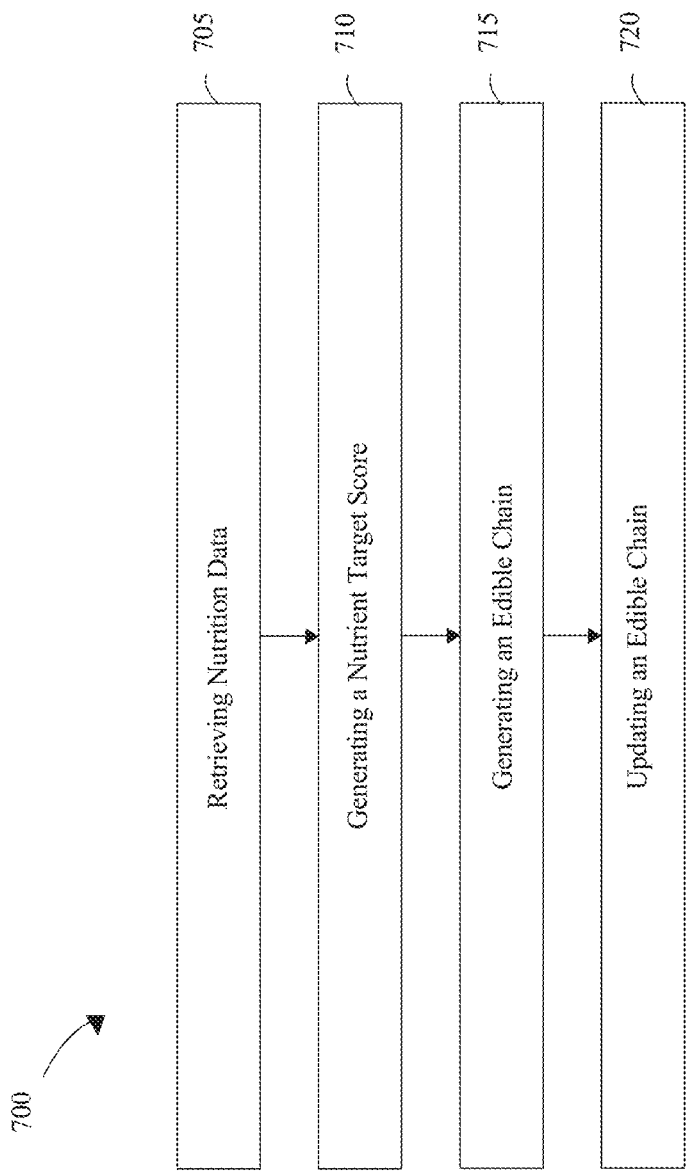
FIG. 7 illustrates a flowchart of another exemplary method for using a feedback loop to optimize meals.

Referring now to FIG. 7, a flowchart of another exemplary method 700 for using a feedback loop to optimize meals. The method 700 includes a step 705 of retrieving, using at least a processor, nutrition data from a database. This may be implemented as disclosed with respect to FIGS. 1-6.

With continued reference to FIG. 7, method 700 includes a step 710 of generating, using at least a processor, a nutrient target score as a function of nutrition data. This may be implemented as disclosed with respect to FIGS. 1-6.

With continued reference to FIG. 7, method 700 includes a step 715 of generating, using at least a processor, an optimization score as a function of nutrition data and the nutrient target score. This may be implemented as disclosed with respect to FIGS. 1-6.

With continued reference to FIG. 7, method 700 includes a step 720 of generating, using at least a processor, an edible chain as a function of the nutrition data and a target nutrient score, wherein the edible chain includes a plurality of ranked edible elements and generating the edible chain includes generating chain training data, wherein the chain training data includes correlations between exemplary nutrition data, exemplary target nutrient scores and exemplary edible chains, training a chain machine-learning model using the chain training data and generating the edible chain using the trained chain machine-learning model. In some embodiments, method 700 may further include generating, using the at least a processor, the plurality of edible elements of the edible chain as a function of an edible quantity and a consumption time interval. In some embodiments, method 700 may further include ranking, using the at least a processor, the plurality of edible elements of the edible chain as a function of a preparation difficulty of the plurality of edible elements. In some embodiments, method 700 may further include determining, using the at least a processor, a nutrition supplement for the edible chain as a function of the nutrition data. In some embodiments, the edible chain may include a plurality of meal plans, wherein each of the plurality of meal plans may include differently ranked edible elements. These may be implemented as disclosed with respect to FIGS. 1-6.

With continued reference to FIG. 7, method 700 includes a step 725 of updating, using at least a processor, an edible chain as a function of a user input received through a user interface, wherein updating the edible chain includes iteratively updating the chain training data on a feedback loop as a function of the updated edible chain. In some embodiments, the user input may include a rank request. In some embodiments, method 700 may further include generating, using the at least a processor, an edible data structure for the edible chain using a large language model. In some embodiments, method 700 may further include iteratively generating, using the at least a processor, subsequent optimization scores as a function of the optimization score. In some embodiments, method 700 may further include modifying, using the at least a processor, the nutrition data as a function of the optimization score, inputting, using the at least a processor, the modified nutrition data into an optimization machine-learning model to output a modified target nutrient score and generating, using the at least a processor, the subsequent optimization scores as a function of the modified nutrition data and the modified target nutrient score. In some embodiments, method 700 may further include updating, using the at least a processor, a phenotype of a user as a function of the optimization score. These may be implemented as disclosed with respect to FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
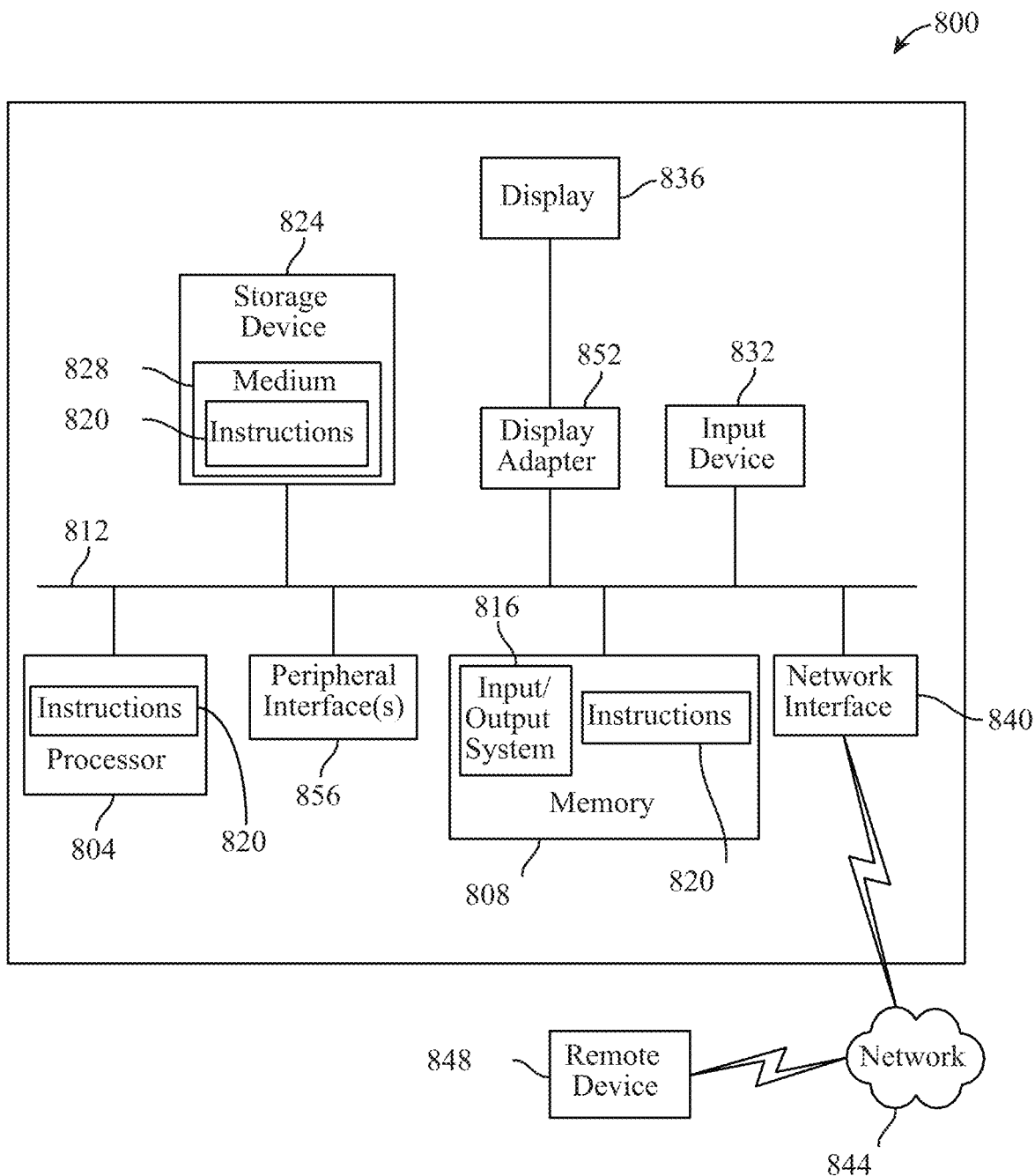
FIG. 8 illustrates a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, apparatuses, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for using a feedback loop to optimize meals, the apparatus comprising:
   at least a processor; and
   a memory communicatively connected to the processor, the memory containing instructions configuring the at least a processor to:
   retrieve nutrition data from a database;
   generate a nutrient target score as a function of the nutrition data;
   generate an optimization score as a function of the nutrition data and the nutrient target score;
   generate an edible chain as a function of the nutrition data and the target nutrient score, wherein the edible chain comprises a plurality of ranked edible elements and generating the edible chain comprises:
      generating chain training data, wherein the chain training data comprises correlations between exemplary nutrition data, exemplary target nutrient scores and exemplary edible chains;
      training a chain machine-learning model using the chain training data; and
      generating the edible chain using the trained chain machine-learning model; and
   update the edible chain as a function of a user input received through a user interface, wherein updating the edible chain comprises:
      iteratively updating the chain training data on a feedback loop as a function of the updated edible chain.

2. The apparatus of claim 1, wherein the memory contains instructions further configuring processor to generate the plurality of edible elements of the edible chain as a function of an edible quantity and a consumption time interval.

3. The apparatus of claim 1, wherein the memory contains instructions further configuring processor to rank the plurality of edible elements of the edible chain as a function of a preparation difficulty of the plurality of edible elements.

4. The apparatus of claim 1, wherein the memory contains instructions further configuring processor to determine a nutrition supplement for the edible chain as a function of the nutrition data.

5. The apparatus of claim 1, wherein the edible chain comprises a plurality of meal plans, wherein each of the plurality of meal plans comprises differently ranked edible elements.

6. The apparatus of claim 1, wherein the memory contains instructions further configuring processor to generate an edible data structure for the edible chain using a large language model.

7. The apparatus of claim 1, wherein the user input comprises a rank request.

8. The apparatus of claim 1, wherein the memory contains instructions further configuring the at least a processor to iteratively generate subsequent optimization scores as a function of the optimization score.

9. The apparatus of claim 8, wherein the memory contains instructions further configuring the at least a processor to:
   modify the nutrition data as a function of the optimization score;
   input the modified nutrition data into an optimization machine-learning model to output a modified target nutrient score; and
   generate the subsequent optimization scores as a function of the modified nutrition data and the modified target nutrient score.

10. The apparatus of claim 1, wherein the memory contains instructions further configuring the at least a processor to update a phenotype of a user as a function of the optimization score.

11. A method for using a feedback loop to optimize meals, the method comprising:
    retrieving, using at least a processor, nutrition data from a database;
    generating, using the at least a processor, a nutrient target score as a function of the nutrition data;
    generating, using the at least a processor, an optimization score as a function of the nutrition data and the nutrient target score;
    generating, using the at least a processor, an edible chain as a function of the nutrition data and the target nutrient score, wherein the edible chain comprises a plurality of ranked edible elements and generating the edible chain comprises:
       generating chain training data, wherein the chain training data comprises correlations between exemplary nutrition data, exemplary target nutrient scores and exemplary edible chains;
       training a chain machine-learning model using the chain training data; and
       generating the edible chain using the trained chain machine-learning model; and
    updating, using the at least a processor, the edible chain as a function of a user input received through a user interface, wherein updating the edible chain comprises:
       iteratively updating the chain training data on a feedback loop as a function of the updated edible chain.

12. The method of claim 11, further comprising:
    generating, using the at least a processor, the plurality of edible elements of the edible chain as a function of an edible quantity and a consumption time interval.

13. The method of claim 11, further comprising:
    ranking, using the at least a processor, the plurality of edible elements of the edible chain as a function of a preparation difficulty of the plurality of edible elements.

14. The method of claim 11, further comprising:
    determining, using the at least a processor, a nutrition supplement for the edible chain as a function of the nutrition data.

15. The method of claim 11, wherein the edible chain comprises a plurality of meal plans, wherein each of the plurality of meal plans comprises differently ranked edible elements.

16. The method of claim 11, further comprising:
generating, using the at least a processor, an edible data structure for the edible chain using a large language model.

17. The method of claim 11, wherein the user input comprises a rank request.

18. The method of claim 11, further comprising:
iteratively generating, using the at least a processor, subsequent optimization scores as a function of the optimization score.

19. The method of claim 18, further comprising:
modifying, using the at least a processor, the nutrition data as a function of the optimization score;
inputting, using the at least a processor, the modified nutrition data into an optimization machine-learning model to output a modified target nutrient score; and
generating, using the at least a processor, the subsequent optimization scores as a function of the modified nutrition data and the modified target nutrient score.

20. The method of claim 11, further comprising:
updating, using the at least a processor, a phenotype of a user as a function of the optimization score.

* * * * *